(12) United States Patent
McKevitt et al.

(10) Patent No.: US 10,998,665 B2
(45) Date of Patent: May 4, 2021

(54) HYBRID CONNECTOR

(71) Applicant: Medline Industries, Inc, Northfield, IL (US)

(72) Inventors: Thomas McKevitt, Oak Lawn, IL (US); Erica Yuen, Skokie, IL (US); Tess Dinterman, Palatine, IL (US)

(73) Assignee: Medline Industries, Inc., Northfield, IL (US)

( * ) Notice: Subject to any disclaimer, the term of this patent is extended or adjusted under 35 U.S.C. 154(b) by 69 days.

(21) Appl. No.: 16/213,850

(22) Filed: Dec. 7, 2018

(65) Prior Publication Data

US 2020/0161796 A1 May 21, 2020

Related U.S. Application Data

(60) Provisional application No. 62/767,956, filed on Nov. 15, 2018.

(51) Int. Cl.
| | |
|---|---|
| *H01R 13/40* | (2006.01) |
| *H01R 13/50* | (2006.01) |
| *H01R 9/24* | (2006.01) |

(52) U.S. Cl.
CPC ........... *H01R 13/50* (2013.01); *H01R 9/2408* (2013.01)

(58) Field of Classification Search
CPC ..................................................... H01R 13/50
USPC .......................................... 439/586, 596–599
See application file for complete search history.

(56) References Cited

U.S. PATENT DOCUMENTS

| | | | |
|---|---|---|---|
| 5,219,185 A | 6/1993 | Oddenino | |
| 6,062,244 A | 5/2000 | Arkans | |
| 6,926,311 B2 | 8/2005 | Chang et al. | |
| 7,490,620 B2* | 2/2009 | Tesluk et al. ........... | F16L 37/23 |
| 7,766,043 B2* | 8/2010 | Thomas et al. ......... | F16K 21/00 |
| 8,092,409 B2 | 1/2012 | Mros et al. | |
| 8,256,459 B2 | 9/2012 | Tesluk et al. | |
| 8,257,286 B2 | 9/2012 | Meyer et al. | |
| 8,784,136 B2 | 7/2014 | Siahaan et al. | |
| 8,801,046 B2* | 8/2014 | Shinoda ................. | F16L 39/00 |
| 9,161,877 B2 | 10/2015 | Mros et al. | |
| D761,427 S | 7/2016 | Patterson et al. | |
| 9,388,929 B2* | 7/2016 | Lewis et al. ........... | F16L 37/56 |
| 9,687,249 B2 | 6/2017 | Hanlon et al. | |
| 9,713,563 B2 | 7/2017 | Mansur, Jr. et al. | |
| D865,662 S | 11/2019 | Ito | |
| 10,476,189 B2 | 11/2019 | Tsubaki | |

(Continued)

OTHER PUBLICATIONS

"Connectors—Pictures and Dimensions", Intermittent and Sequential Connector Examples provided by Inventors; Used in Medline's Hemo-Force Technology; Generation 1 and 2; Unknown Publication Date but prior to filing of present application.

(Continued)

*Primary Examiner* — Khiem M Nguyen
(74) *Attorney, Agent, or Firm* — Philip H. Burrus, IV

(57) ABSTRACT

A connector (100) includes a body (101) and a plurality of ports (102,103,104) extending distally from a front major face (301) of the body. The body defines a connector bay (320) configured to couple to any of a single-tube, intermittent, deep vein thrombosis therapy male connector (901), a double-tube, intermittent, deep vein thrombosis therapy male connector (902), or a three-tube, sequential, deep vein thrombosis therapy male connector (903).

20 Claims, 9 Drawing Sheets

(56) References Cited

U.S. PATENT DOCUMENTS

| | | |
|---|---|---|
| 10,490,932 B1 | 11/2019 | Schneider et al. |
| D877,080 S | 3/2020 | Tabata |
| 2012/0109030 A1 | 5/2012 | Mros et al. |

OTHER PUBLICATIONS

Gottschalk, Darcey, "NonFinal Office Action", U.S. Appl. No. 29/676,121, filed Jan. 8, 2019; dated Apr. 28, 2020.

* cited by examiner

HYBRID CONNECTOR

CROSS REFERENCE TO PRIOR APPLICATIONS

This application claims priority and benefit under 35 U.S.C. § 119(e) from U.S. Provisional Application No. 62/767,956, filed Nov. 15, 2018, which is incorporated by reference for all purposes.

BACKGROUND

Technical Field

This disclosure relates generally to connectors, and more particularly to connectors for medical applications.

Background Art

Connectors are used in medical applications to deliver air or other fluids from compression equipment to medical therapy devices. It would be advantageous to have an improved connector.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present disclosure.

Figure 1:
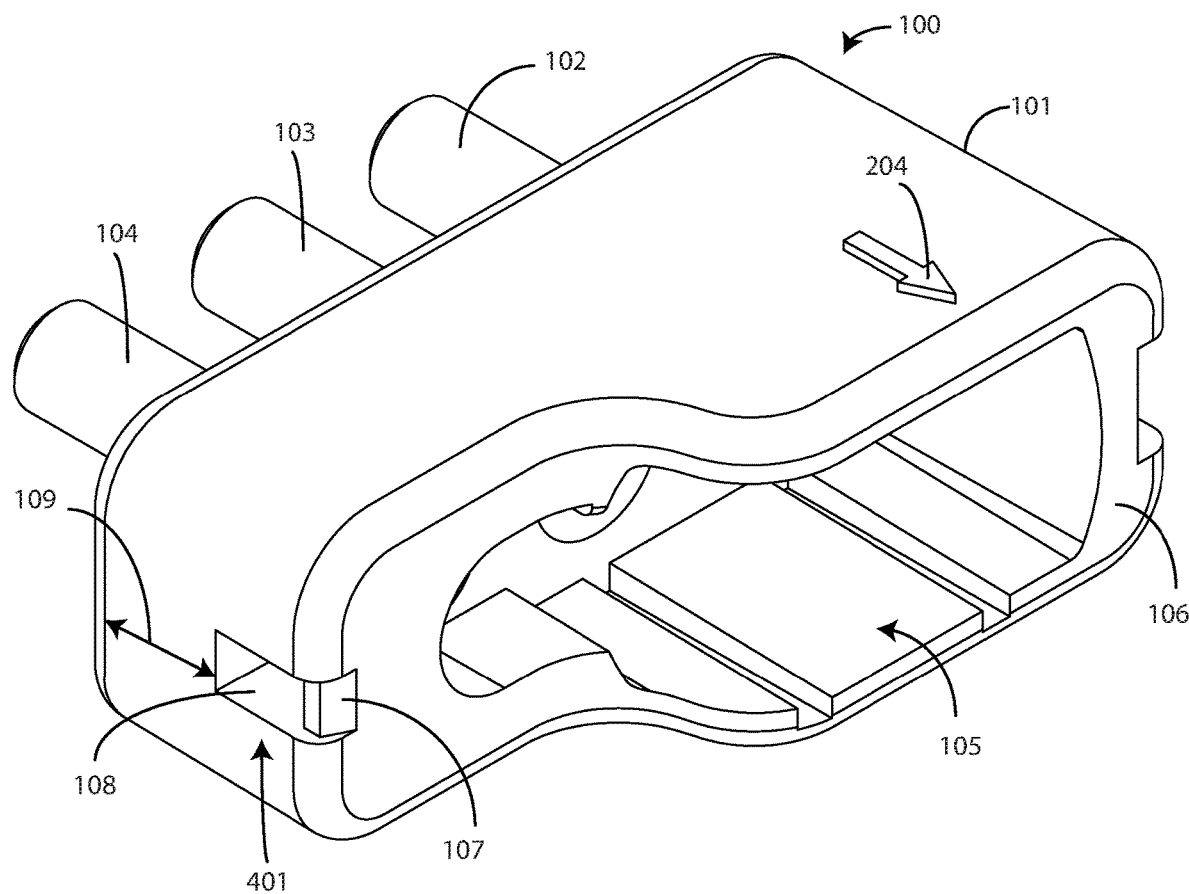
FIG. 1 illustrates a perspective view of one illustrative connector in accordance with one or more embodiments of the disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION OF THE DRAWINGS

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions.

As used herein, components may be "operatively coupled" when information can be sent between such components, even though there may be one or more intermediate or intervening components between, or along the connection path. The terms "substantially" and "about" are used to refer to dimensions, orientations, or alignments inclusive of manufacturing tolerances. Thus, a "substantially orthogonal" angle with a manufacturing tolerance of plus or minus two degrees would include all angles between 88 and 92, inclusive. Also, reference designators shown herein in parenthesis indicate components shown in a figure other than the one in discussion. For example, talking about a device (10) while discussing figure A would refer to an element, 10, shown in figure other than figure A.

Compression devices are frequently used in medical therapy treatments. For pneumatic compression devices, air is delivered from a distant pump to a device attached to a patient. Illustrating by example, in deep vein thrombosis therapy, an air pump is connected via one or more flexible, hollow, air supply tubes to a compressive garment that is positioned about a patient's limb. The air pump then inflates and deflates the compressive garment by delivering, and withdrawing, air to and from the compressive garment via one or more flexible tubes. This inflation and deflation of the compressive garment works to prevent blood clots from enlarging in size, as well as preventing existing clots from breaking free in the circulatory system, thereby potentially causing a pulmonary embolism.

The flexible tubes, be they one, two, or three, couple to both the pump and the compressive garment using a connector. Air is then transferred to or from the compressive garment to selectively inflate and deflate the compressive garment. This selective compression and decompression limits blood "stasis," thereby preventing clots or "thrombi" from enlarging. This therapy is especially beneficial when a patient is inactive for lengthy periods of time.

There are generally two types of compressive garments used in deep vein thrombosis therapy. The first is known as an "intermittent" compressive garment and includes one bladder. A pump supplies air through to and from the single bladder through a single flexible tube in one embodiment. In another embodiment, a pump uses a pair of flexible air supply tubes, with one delivering air to the single bladder of compressive garment and another removing the air from the single bladder of the compressive garment. In either case, a first connector couples the one or two tubes to the pump, while a second connector couples the one or two tubes to the compressive garment.

The second type of compressive garment is known as a "sequential" compressive garment and includes three bladders. Since three bladders are employed, three flexible tubes are required to deliver air to each bladder sequentially. A first connector couples the three tubes to the compressive garment, while a second connector couples the three tubes to the pump.

The fact that the intermittent system uses either one flexible tube or two, while the sequentially system uses three, causes a problem in that different pumps are required for each system. Thus, if a particular patient begins treatment using an intermittent system, but then switches to a sequential system, the health care provider needs to not only change the compressive garment but also obtain a completely different pump and coupling system. This takes time and increases health care costs.

Embodiments of the disclosure advantageously solve this problem by providing a connector that couples to a single pump, but that accommodates flexible tubing systems that attach to either intermittent compressive garments or sequential compressive garments. In one or more embodiments, a connector comprises a body and three ports. In one or more embodiments, the three ports extend distally from a front major face of the body. In one or more embodiments, the body defines a planar-concave-convex-planar rear surface. Advantageously, the inclusion of the planar-concave-convex-planar rear surface allows the connector to couple to any of a single-tube, intermittent, deep vein thrombosis therapy male connector, a double-tube, intermittent, deep vein thrombosis therapy male connector, or a three-tube, sequential, deep vein thrombosis therapy male connector.

In one or more embodiments, a connector comprises a body and one or more ports extending distally from a front major face of the body. In one or more embodiments, a rear face of the body defines a connector bay. In one or more embodiments, the connector bay comprises a first upper surface, a second upper surface, a hemispherical side surface, and a curvilinear side surface. In one or more embodiments, an extension spur separating the first upper surface and the second upper surface. Advantageously, the extension spur retains a single-tube, intermittent, deep vein thrombosis therapy male connector within the connector bay, while also allowing either a double-tube, intermittent, deep vein thrombosis therapy male connector or a three-tube, sequential, deep vein thrombosis therapy male connector to insert into the connector bay as well.

Not only do embodiments of the disclosure allow both intermittent compressive garments and sequential compressive garments to couple to a single pump, they also ensure that a secure, non-leaking seal is formed between the flexible tubing leading to the compressive garment and the pump itself. The connector advantageously provides an airtight seal between sealing surfaces of any of a one-tube intermittent male connector, a two-tube intermittent male connector, or a three-tube sequential male connector. The connections between any of the three male connectors and the connector of the present disclosure are fluid tight.

Figure 6:
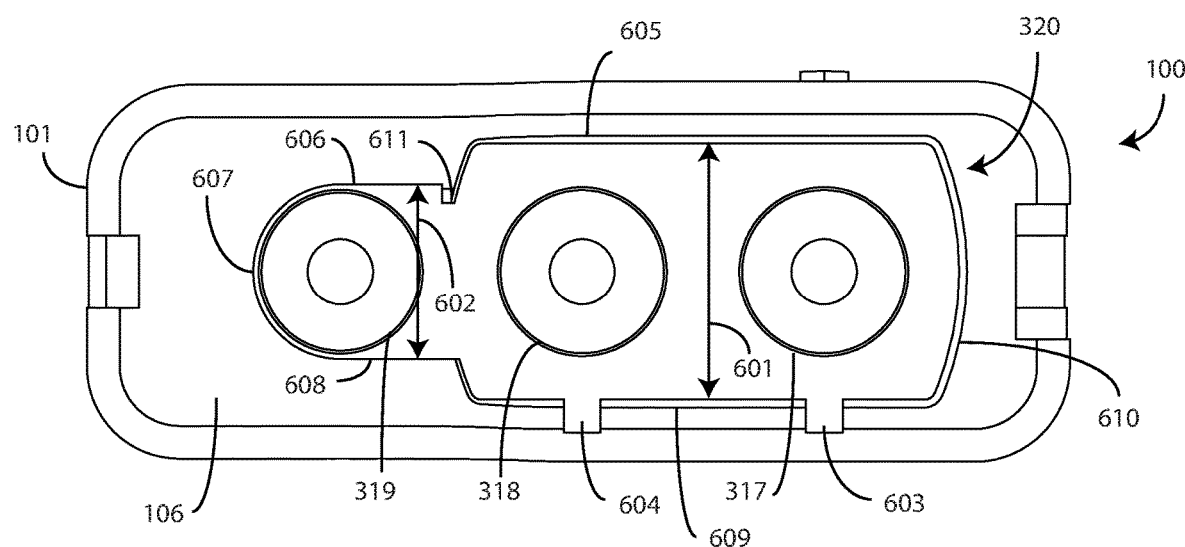
FIG. 6 illustrates a rear elevation view of one explanatory connector in accordance with one or more embodiments of the disclosure.
Figure 7:
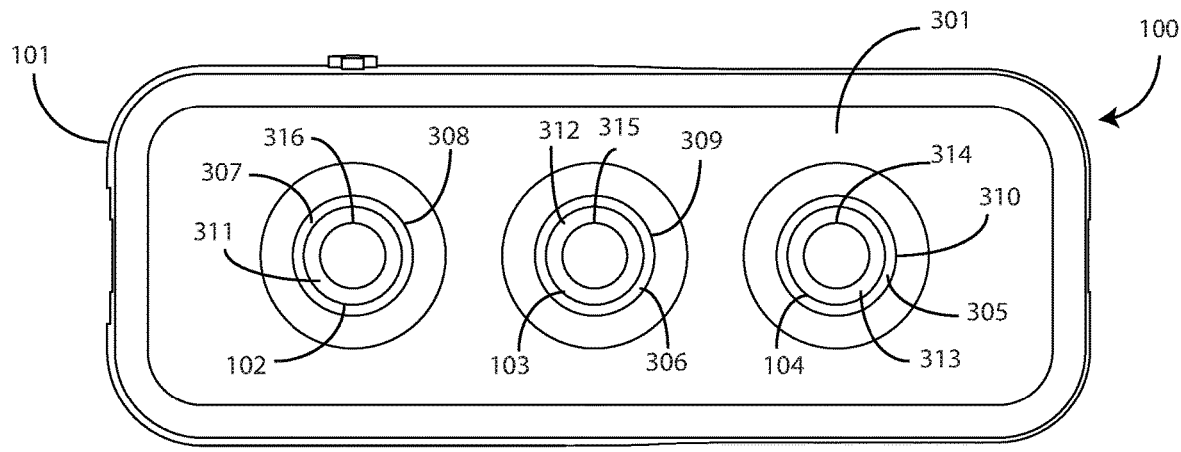
FIG. 7 illustrates a front elevation view of one explanatory connector in accordance with one or more embodiments of the disclosure.

Turning now to FIGS. 1-8, illustrated therein is one explanatory connector 100 configured in accordance with one or more embodiments of the disclosure. In one or more embodiments, the connector 100 includes a body 101 and three ports 102,103,104. In the illustrative embodiment of FIGS. 1-8, the three ports 102,103,104 are cylindrical in cross section, as shown in FIG. 7. However, in other embodiments the three ports 102,103,104 can have different cross-sectional shapes. Examples of such alternate cross-sectional shapes include squares, hexagons, triangles, ovals, or keyed shapes. Other cross-sectional shapes for the three ports 102,103,104 will be obvious to those of ordinary skill in the art having the benefit of this disclosure.

In the illustrative embodiment of FIGS. 1-8, the three ports 102,103,104 extend distally from a front major face 301 of the body 101 of the connector 100. In this illustrative embodiment, each of the three ports 102,103,104 includes an expanding base 302,303,304 that expands radially outward as the three ports 102,103,104 engage the front major face 301 of the body 101 of the connector 100. This expansion of the three ports 102,103,104 at their base, i.e., at the engagement between the three ports 102,103,104 and the front major face 301 of the body 101 of the connector 100 ensures that a fluid-tight seal occurs between the pump when the three ports 102,103,104 are inserted into apertures on the pump.

In one or more embodiments, the three ports 102,103,104 also include a tapering lead edge 305,306,307 that spans a sidewall 308,309,310 of each of the three ports 102,103,104 and a terminating face 311,312,313 of each of the three ports 102,103,104. The tapering lead edge 305,306,307 makes insertion of the three ports 102,103,104 into apertures of a pump simpler.

In one or more embodiments, each of the three ports 102,103,104 defines a lumen 314,315,316 through which air can pass. In one or more embodiments, each lumen 314, 315,316 extends from the terminating face 311,312,313 of each of the three ports 102,103,104 to a connector bay 105 that is open at a rear major face 106 of the connector 100. Each lumen 314,315,316 permits air to pass to and from the pump to a connector coupled to the connector bay 105 in one or more embodiments.

In one or more embodiments, each lumen 314,315,316 intersects a female coupler 317,318,319 that is centrally situated within the body 101 of the connector 100. The female coupler 317,318,319 is configured to receive a male connector coupled to flexible tubing, which is then coupled to a compressible garment. In one embodiment, where a single-tube, intermittent, male connector couples to the connector 100, it couples to female coupler 319. When a double-tube, intermittent, male connector couples to the connector 100, a first male connector couples to female coupler 317, while a second male connector couples to female coupler 318. When a three-tube, sequential male connector couples to the connector, a first male connector couples to female coupler 317, while a second male connector couples to female coupler 318. A third male connector then couples to female coupler 319.

In one or more embodiments, each female coupler 317, 318,319 bridges its corresponding lumen 314,315,316 and a connector bay 320. As best shown in FIG. 6, the connector bay 320 defines an aperture having two different heights 601,602. The portion of the aperture that bounds the first female coupler 317 and the second female coupler 318 defines a first height 601, while the portion of the aperture that bounds the third female coupler 319 defines a second height 602. In this illustrative embodiment, the second height 602 is less than the first height 601.

In one or more embodiments the aperture of the connector bay 320 defines one or more rail receivers 603,604 along a bottom surface. In the illustrative embodiment of FIGS. 1-8, the aperture of the connector bay 320 defines two rail receivers 603,604. Each rail receiver 603,604 is configured to receive a rail of a double-tube, intermittent, male connector when that connector couples to the connector 100, with a first male connector engaging female coupler 317 and a second male connector engaging female coupler 318. More or fewer rail receivers can be included as will be obvious to those of ordinary skill in the art having the benefit of this disclosure.

In one or more embodiments, the aperture of the connector bay 320 includes a first upper surface 605, a second upper surface 606, a hemispherical side surface 607, a lower surface 609, and a curvilinear side surface 610. In this illustrative embodiment, an extension spur 611 separates the first upper surface 605 and the second upper surface 606. In one or more embodiments, the extension spur 611 retains the single-tube, intermittent, male connector within the connector bay 320 when the same couples to the connector 100 and, correspondingly, to female coupler 319.

Figure 3:
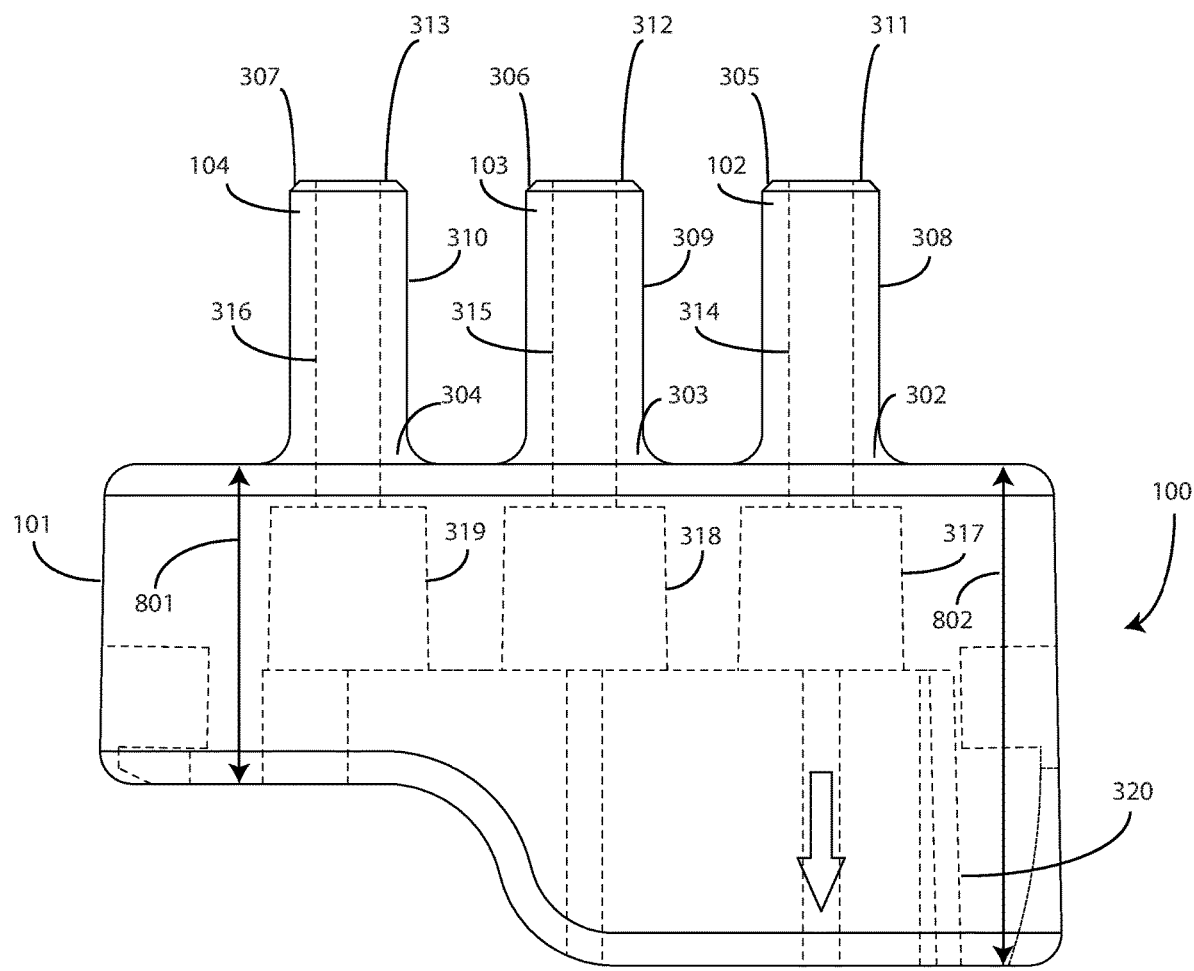
FIG. 3 illustrates a top plan view of one explanatory connector in accordance with one or more embodiments of the disclosure.
Figure 4:
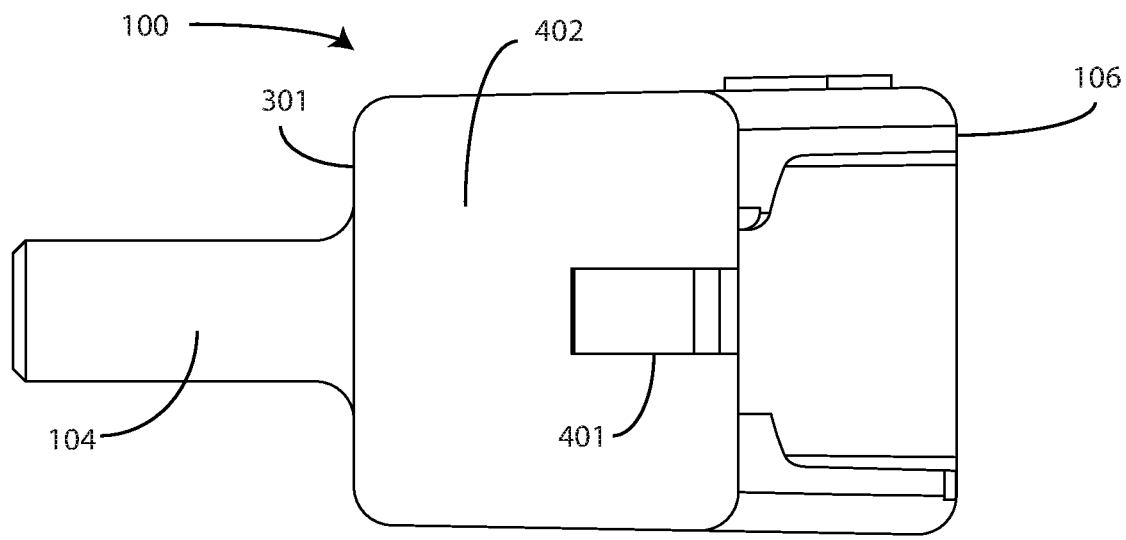
FIG. 4 illustrates a left side elevation view of one explanatory connector in accordance with one or more embodiments of the disclosure.
Figure 5:
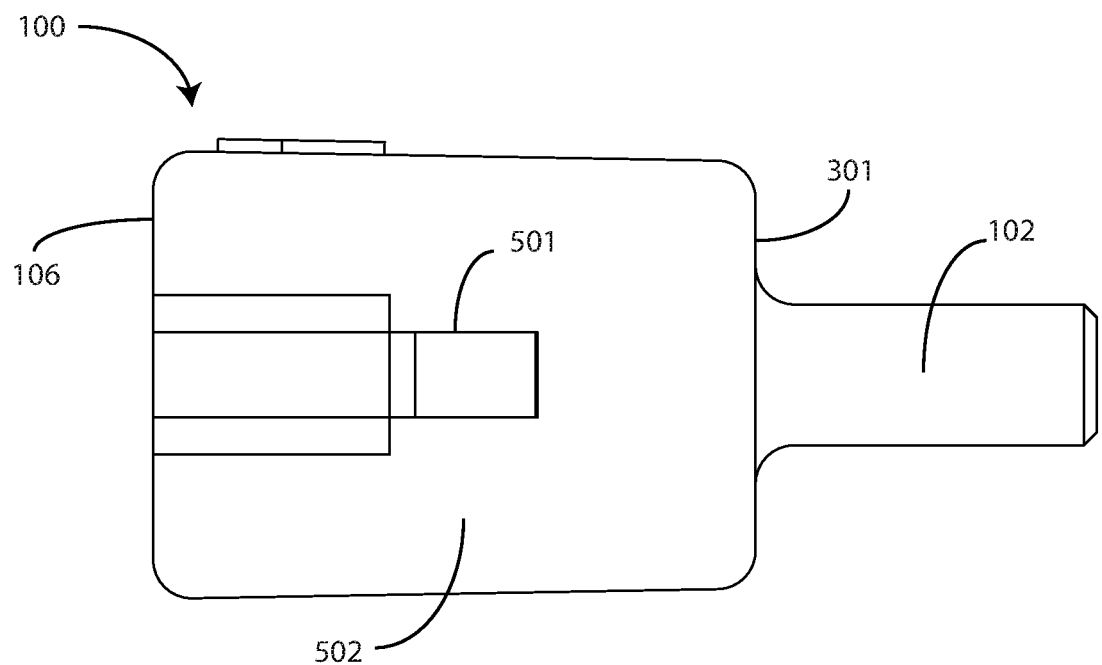
FIG. 5 illustrates a right side elevation view of one explanatory connector in accordance with one or more embodiments of the disclosure.
Figure 8:
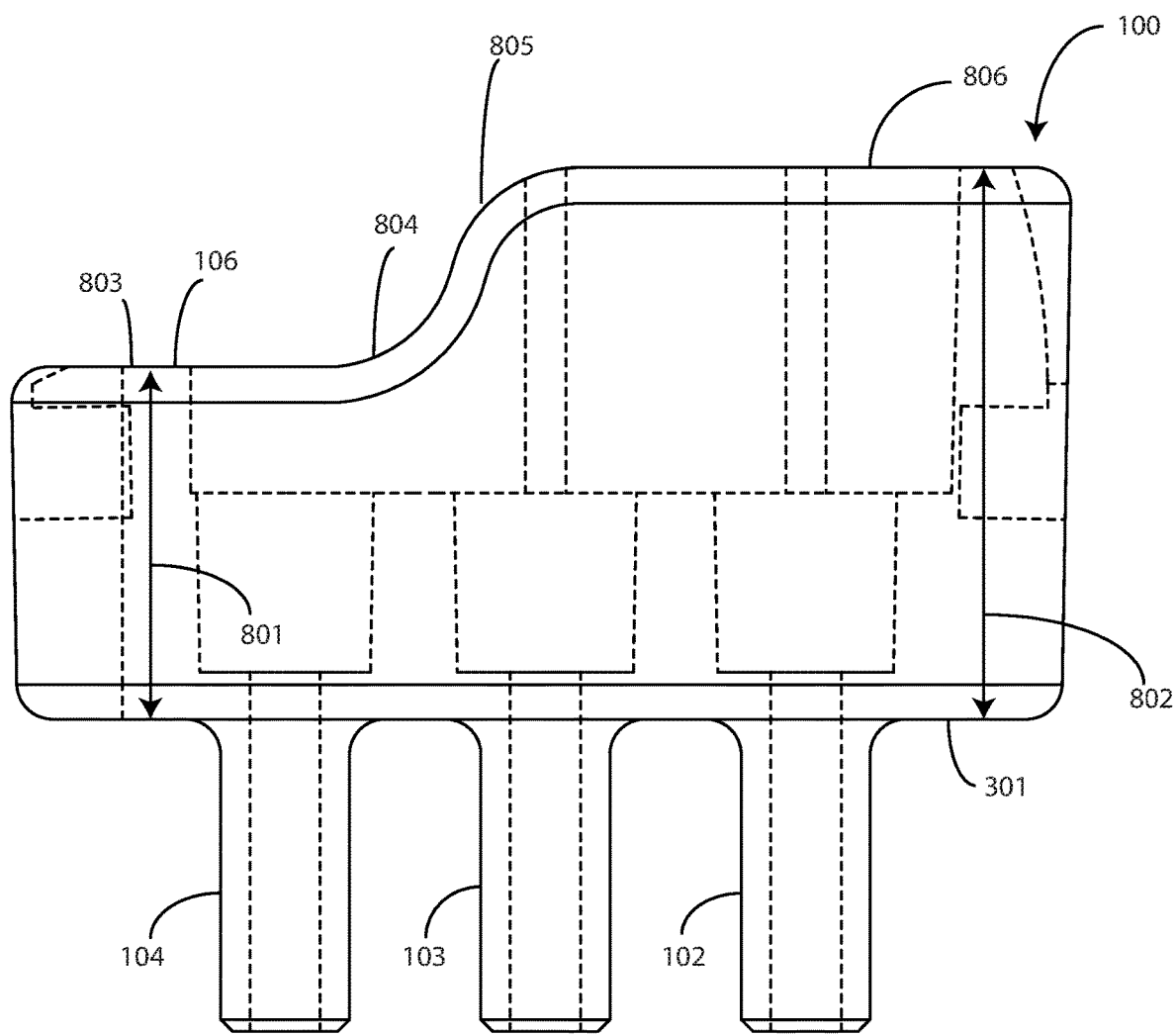
FIG. 8 illustrates a bottom plan view of one explanatory connector in accordance with one or more embodiments of the disclosure.

As best shown in FIGS. 3 and 8, in one or more embodiments the rear major face 106 of the connector defines a planar-concave-convex-planar rear surface defining two depths 801,802 of the body 101 of the connector 100. The planar-concave-convex-planar rear surface is defined by a first planar surface 803, a concave surface 804, a convex surface 805, and a second planar surface 806. In this illustrative embodiment, the concave surface 804 connects the first planar surface 803 and the convex surface 805. The convex surface 805 connects the concave surface 804 and the second planar surface 806.

In this illustrative embodiment, the third lumen 316 and the third female coupler 319 engage the connector bay 320 and traverse the body 101 of the connector 100 where the depth 801 is shorter. By contrast, the first lumen 314 and its corresponding first female coupler 317, and the second lumen 315 and its corresponding second female coupler 318, engage the connector bay 320 and traverse the body 101 of the connector 100 where the depth 802 is longer in this illustrative embodiment.

Mechanical latch engagements 401,501 can be disposed on either exterior sidewall 402,502 in one or more embodiments. While disposed on the left and right exterior sidewalls 402,502 in the illustrative embodiment of FIGS. 1-8, they could be disposed on the upper and lower exterior faces as well.

Figure 2:
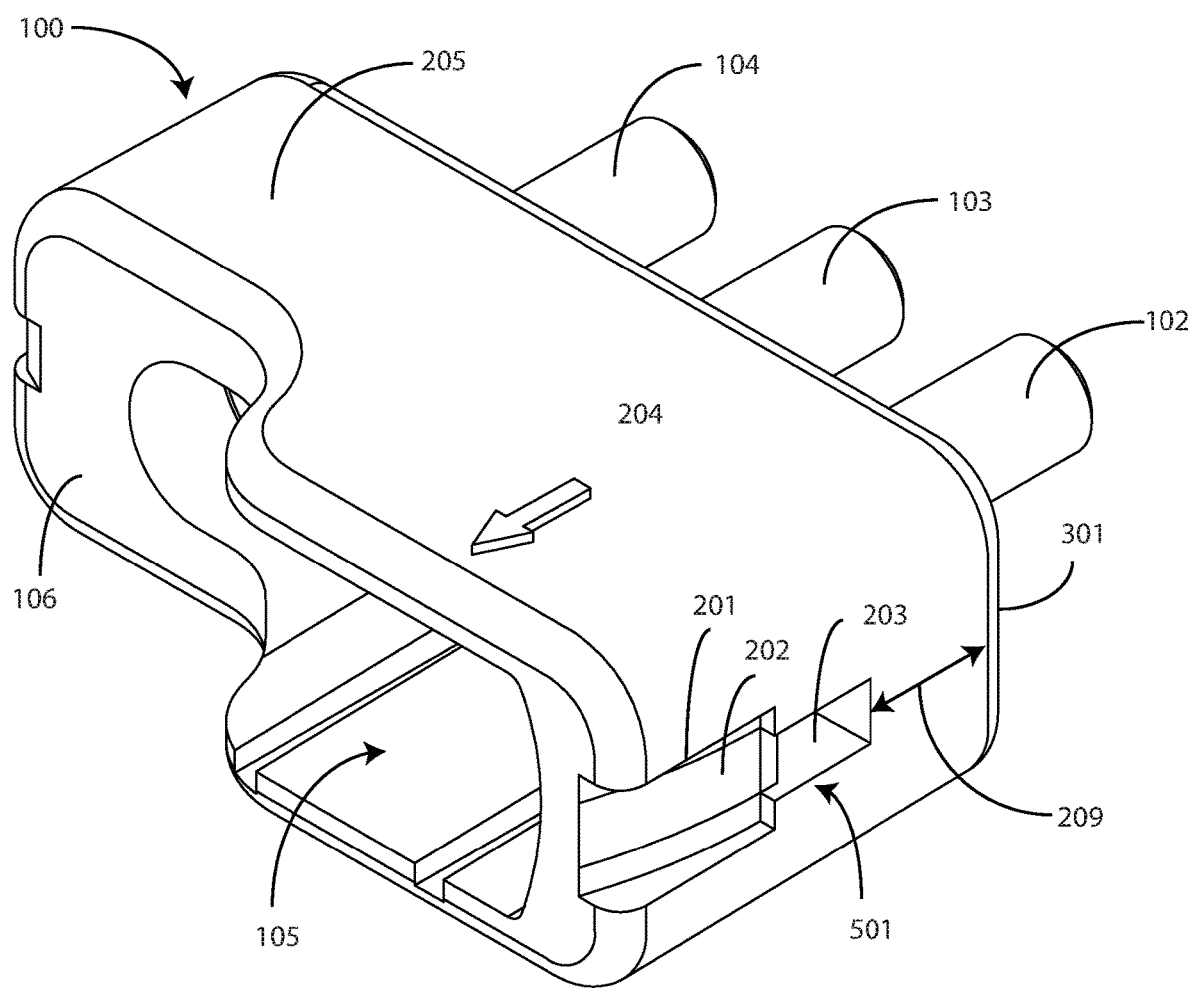
FIG. 2 illustrates another perspective view of one explanatory connector in accordance with one or more embodiments of the disclosure.

As best shown in FIG. 2, in one or more embodiments mechanical latch engagement 501 comprises a receiving bay 201 defining an inclined ramp 202 along its interior base surface. At the end of inclined ramp 202, a latch receiver 203 extends into the body 101 of the connector 100. As shown in FIG. 2, in one or more embodiments the latch receiver 203 has both a height and width that is less than that of the receiving bay 201.

As best shown in FIG. 1, in one or more embodiments mechanical latch engagement 401 includes a ramp stub 107 that stands as a barrier to entry into a latch receiver 108 that extends into the body 101 of the connector 100. The ramp stub 107 of this illustrative embodiment is another inclined ramp, but is steeper and shorter than is the inclined ramp 202 of mechanical latch engagement 501.

In one or more embodiments, the distance 109 between the front major face 301 and the latch receiver 108 disposed on the left side of the body 101 of the connector 100 is the same as the distance 209 between the front major face 301 and the latch receiver 203 situated on the right side of the body 101 of the connector. This common distance allows latches of a three-tube, sequential male connector to engage latch receiver 108 and latch receiver 203, respectively, when the three-tube, sequential male connector couples to the connector 100 with a first male connector coupling to female coupler 317, a second male connector coupling to female coupler 318, and a third male connector coupling to female coupler 319.

In one or more embodiments, visual indicia can be disposed on the exterior surfaces of the body 101 of the connector 100. In this illustrative embodiment, an arrow 204 indicating which way air flows through the lumens 3314, 315,316 is placed atop the upper surface 205 of the body 101 of the connector 100. This arrow 204 advantageously provides a quick indication illustrating how to connect the connector 100 to a pump and another connector, be it any of a single-tube, intermittent, male connector, a double-tube, intermittent, male connector, or a three-tube, sequential male connector. Other types of indicia suitable for placement on the body 101 of the connector 100 will be obvious to those of ordinary skill in the art having the benefit of this disclosure.

The connector 100 can be manufactured from any of a variety of materials. Illustrating by example, in one embodiment the connector 100 is manufactured from polyvinylchloride. In another embodiment, the connector 100 is manufactured from polyurethane. In still another embodiment, the connector 100 is manufactured from silicone. In yet another embodiment, the connector 100 is manufactured from latex rubber. These materials are illustrative only, as numerous others will be obvious to those of ordinary skill in the art having the benefit of this disclosure.

Figure 9:
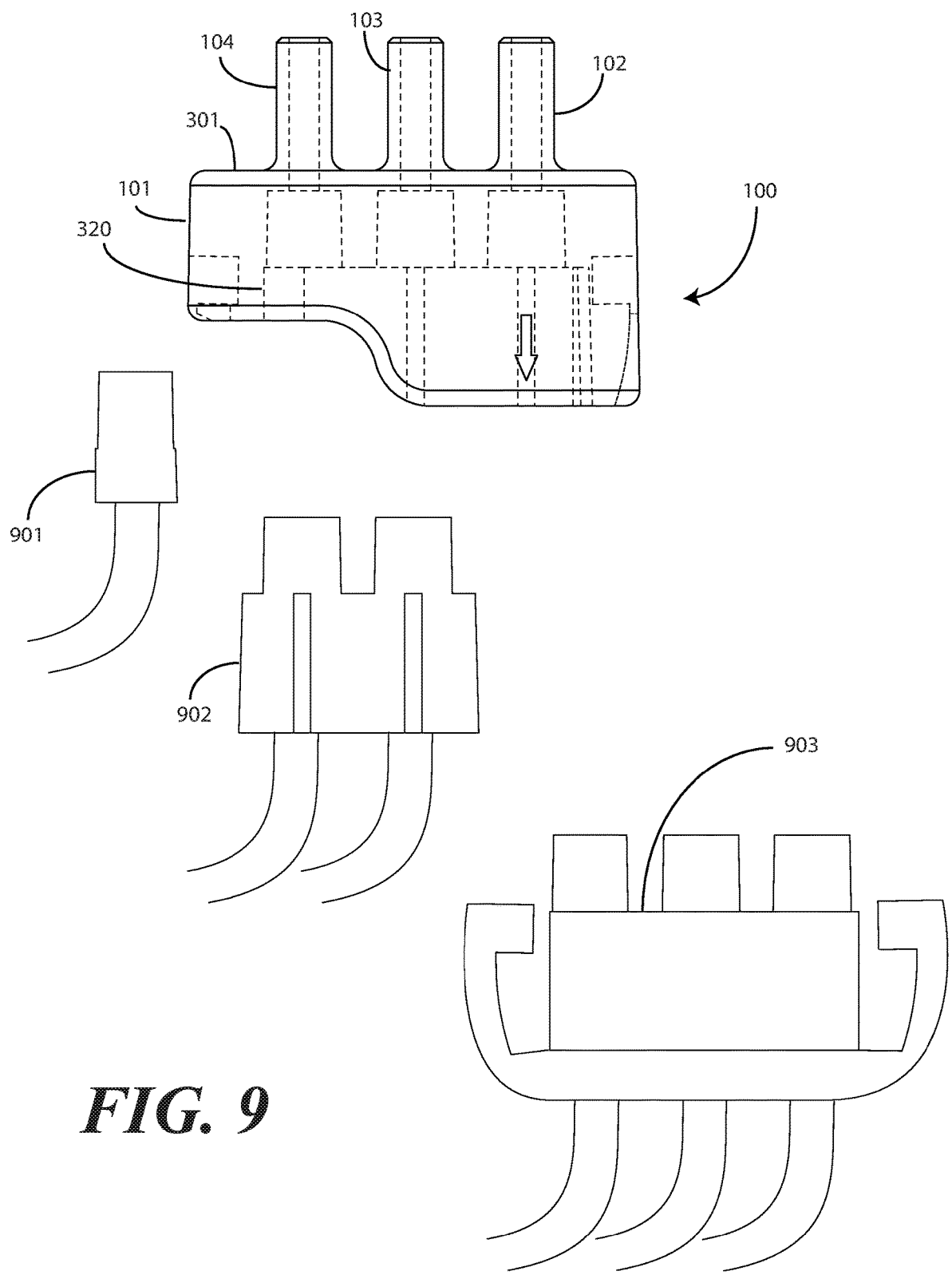
FIG. 9 illustrates one explanatory connector and the various connectors to which it can be coupled in accordance with one or more embodiments of the disclosure.

Turning now to FIG. 9, illustrated therein are various embodiments of the disclosure. As shown, a connector 100 configured in accordance with embodiments of the disclosure includes a body 101. The connector 100 also includes a plurality of ports 102,103,104 extending distally from a front major face 301 of the body 101.

Figure 10:
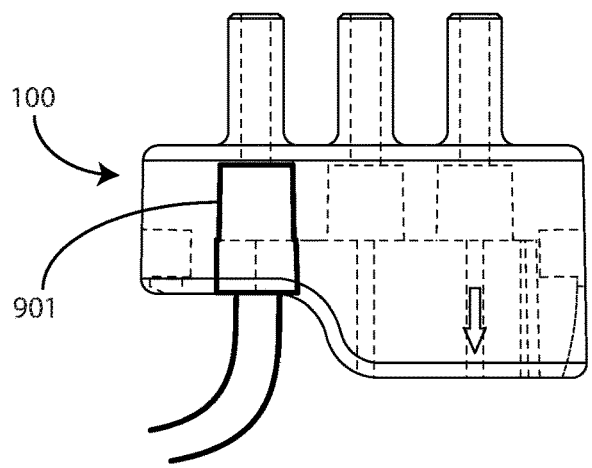
FIG. 10 illustrates one explanatory connector in accordance with one or more embodiments of the disclosure coupled to a first connector type.
Figure 11:
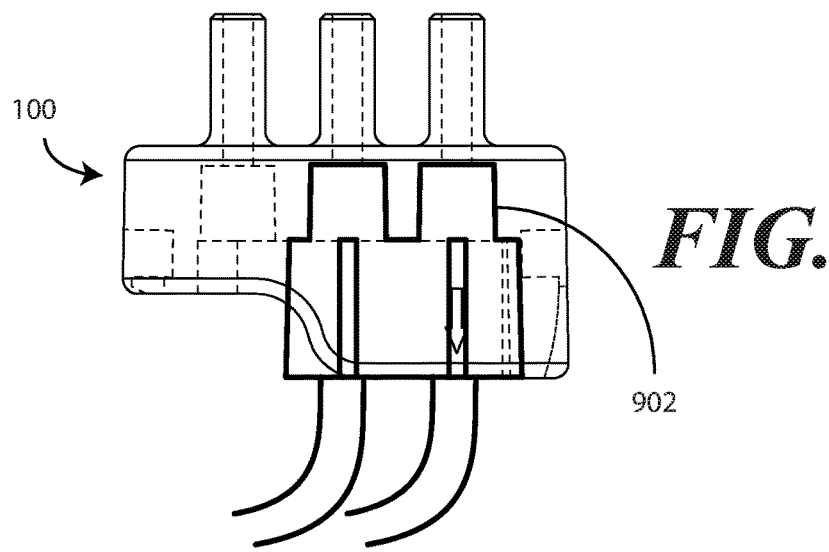
FIG. 11 illustrates one explanatory connector in accordance with one or more embodiments of the disclosure coupled to a second connector type.

As described above, in one or more embodiments, the body 101 defines a connector bay 320 that configured to couple to any of a single-tube, intermittent, deep vein thrombosis therapy male connector 901, a double-tube, intermittent, deep vein thrombosis therapy male connector 902, or a three-tube, sequential, deep vein thrombosis therapy male connector 903. The connector 100 is shown coupled to the single-tube, intermittent, deep vein thrombosis therapy male connector 901 in FIG. 10. The connector 100 is shown coupled to the double-tube, intermittent, deep vein thrombosis therapy male connector 902 in FIG. 11. The connector 100 is shown coupled to the three-tube, sequential, deep vein thrombosis therapy male connector 903 in FIG. 12.

Figure 12:
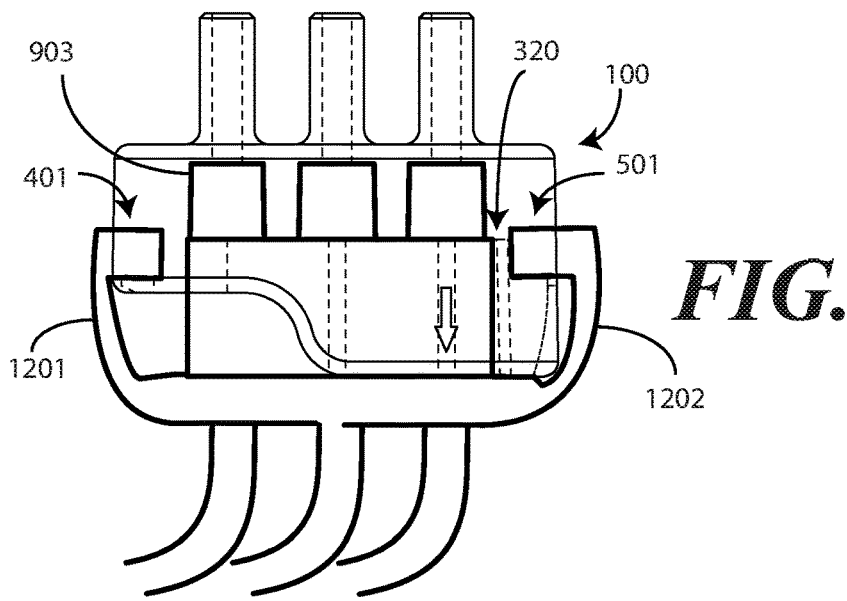
FIG. 12 illustrates one explanatory connector in accordance with one or more embodiments of the disclosure coupled to a third connector type.

As shown in FIG. 9, in one or more embodiments the body 101 defines one or more mechanical latch engagements 401,501. As shown in FIG. 12, the one or more mechanical latch engagements 401,501 are configured to receive latches 1201,1202 of the three-tube, sequential, deep vein thrombosis therapy male connector 903 when the three-tube, sequential, deep vein thrombosis therapy male connector 903 couples to the connector bay 320.

Figure 13:
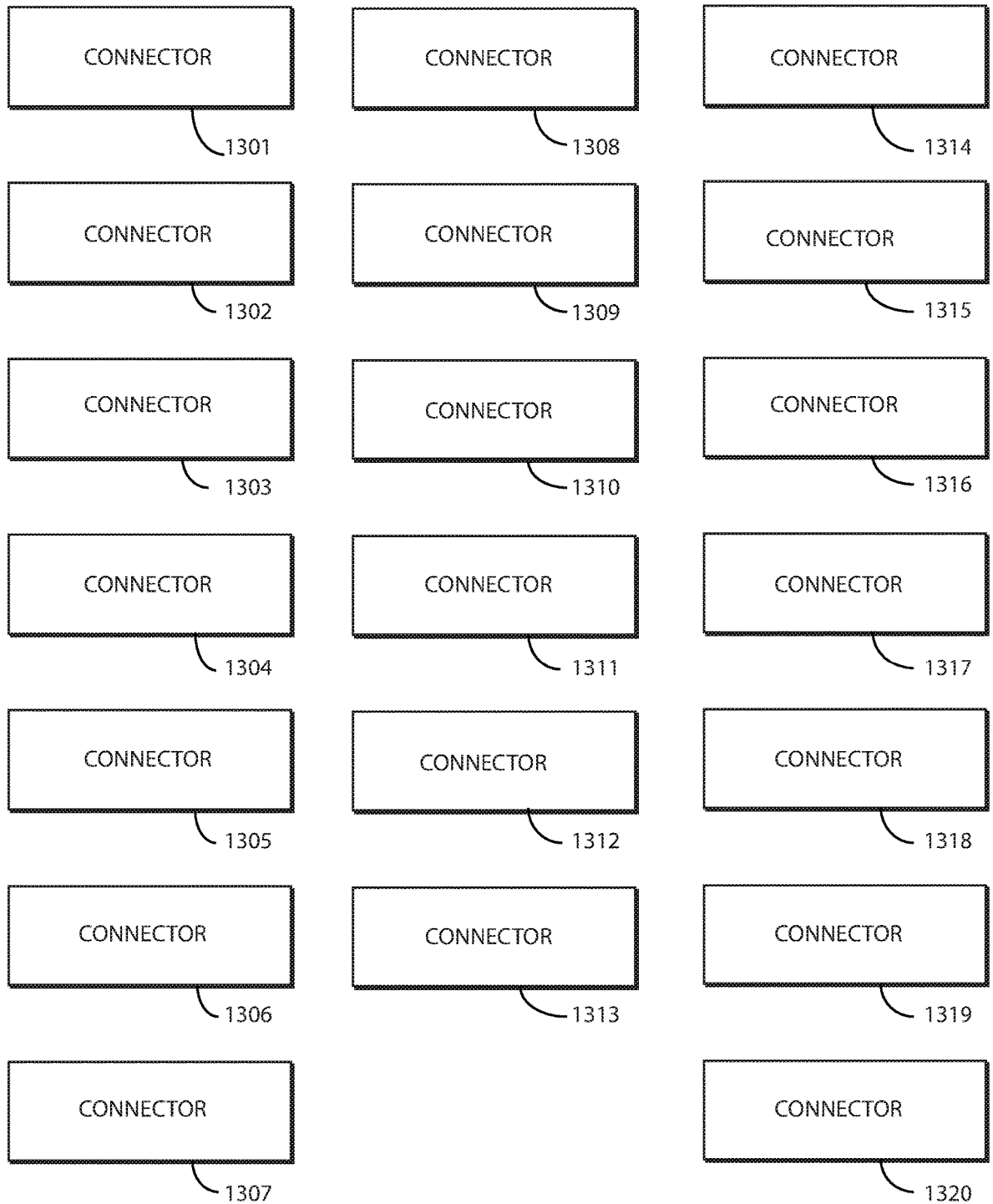
FIG. 13 illustrates various embodiments of the disclosure.

Turning now to FIG. 13, illustrated therein are various embodiments of the disclosure. At 1301, a connector comprises a body. At 1301, three ports extend distally from a front major face of the body. At 1301, the body defines a planar-concave-convex-planar rear surface.

At 1302, the planar-concave-convex-planar rear surface of 1301 comprises a first planar surface, a concave surface, a convex surface, and a second planar surface. At 1303, the concave surface of 1302 connects the first planar surface and the convex surface. At 1304, the convex surface of 1303 connects the concave surface and the second planar surface.

At 1305, the body of 1301 further comprises one or more mechanical latch engagements along an exterior of the body. At 1306, the one or more mechanical latch engagements of 1305 comprise a first mechanical latch engagement. At 1306, the first mechanical latch engagement comprises a receiving bay defining an inclined ramp along an interior base surface of the receiving bay. At 1306, the first mechanical latch engagement comprises a latch receiver situated at an end of the inclined ramp.

At 1307, the one or more mechanical latch engagements of 1306 further comprise a second mechanical latch engagement. At 1307, the second mechanical latch engagement comprises a ramp stub and another latch receiver. At 1308, the latch receiver and the another latch receiver of 1307 are situated a common distance from the front major face of the body. At 1309, a depth of the body of 1302 between the front major face and the first planar surface is less than another depth of the body between the front major face and the second planar surface.

At 1310, a connector comprises a body and one or more ports extending distally from a front major face of the body. At 1310, a rear face of the body defines a connector bay. At 1310, the connector bay comprises a first upper surface, a second upper surface, a hemispherical side surface, and a curvilinear side surface. At 1310, the connector bay further comprises an extension spur separating the first upper surface and the second upper surface.

At 1311, the connector bay of 1310 further comprises a lower surface defining one or more rail receivers. At 1312, each port of the connector of 1310 defines a lumen passing from a terminating face of the each port to a corresponding female coupler.

At 1313, the one or more ports of 1312 comprise three ports. At 1313, a first port defines a first lumen passing from a first terminating face to a first female coupler. At 1313, a second port defines a second lumen passing from a second terminating face to a second female coupler. At 1313, a third port defines a third lumen passing from a third terminating face to a third female coupler.

At 1314, the connector bay of 1313 defines an aperture having at least two different heights. At 1315, a portion of the aperture bounding the first female coupler and the second female coupler defines a first height, while another portion of the aperture bounding the third female coupler defines a second height. At 1316, the second height of 1315 is less than the first height.

At 1317, a connector comprises a body and a plurality of ports extending distally from a front major face of the body. At 1317, the body defines a connector bay configured to couple to any of a single-tube, intermittent, deep vein thrombosis therapy male connector, a double-tube, intermittent, deep vein thrombosis therapy male connector, or a three-tube, sequential, deep vein thrombosis therapy male connector.

At 1318, the connector of 1317 further comprises one or more mechanical latch engagements configured to receiving latches of the three-tube, sequential, deep vein thrombosis therapy male connector when the three-tube, sequential, deep vein thrombosis therapy male connector couples to the connector bay. At 1319, the connector of 1317 further comprises visual indicia disposed on an exterior surface of the body. At 1320, the visual indicia of 1318 comprise an arrow indicating an airflow direction through the plurality of ports.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims. For example, in one or more embodiments the connector 100 can be color-coded to indicate to which pump it should be connected. Accordingly, the specification and figures are to be regarded in an illustrative rather than a restrictive sense, and all such modifications are intended to be included within the scope of present disclosure. The benefits, advantages, solutions to problems, and any element(s) that may cause any benefit, advantage, or solution to occur or become more pronounced are not to be construed as a critical, required, or essential features or elements of any or all the claims.

What is claimed is:

1. A connector, comprising:
   a body; and
   three ports extending distally from a front major face of the body;
   wherein the body defines a planar-concave-convex-planar rear surface.

2. The connector of claim 1, the planar-concave-convex-planar rear surface comprising:
   a first planar surface;
   a concave surface;
   a convex surface; and
   a second planar surface.

3. The connector of claim 2, the concave surface connecting the first planar surface and the convex surface.

4. The connector of claim 3, the convex surface connecting the concave surface and the second planar surface.

5. The connector of claim 1, the body further comprising one or more mechanical latch engagements along an exterior of the body.

6. The connector of claim 5, the one or more mechanical latch engagements comprising a first mechanical latch engagement comprising a receiving bay defining an inclined ramp along an interior base surface of the receiving bay and a latch receiver situated at an end of the inclined ramp.

7. The connector of claim 6, the one or more mechanical latch engagements further comprising a second mechanical latch engagement comprising a ramp stub and another latch receiver.

8. The connector of claim 7, the latch receiver and the another latch receiver situated a common distance from the front major face of the body.

9. The connector of claim 2, wherein a depth of the body between the front major face and the first planar surface is less than another depth of the body between the front major face and the second planar surface.

10. A connector, comprising:
    a body;
    one or more ports extending distally from a front major face of the body;
    wherein a rear face of the body defines a connector bay comprising a first upper surface, a second upper surface, a hemispherical side surface, and a curvilinear side surface;

further comprising an extension spur separating the first upper surface and the second upper surface.

11. The connector of claim 10, the connector bay further comprising a lower surface defining one or more rail receivers.

12. The connector of claim 10, each port of the one or more ports defining a lumen passing from a terminating face of the each port to a corresponding female coupler.

13. The connector of claim 12, the one or more ports comprising three ports, wherein:
 a first port defines a first lumen passing from a first terminating face to a first female coupler;
 a second port defines a second lumen passing from a second terminating face to a second female coupler; and
 a third port defines a third lumen passing from a third terminating face to a third female coupler.

14. The connector of claim 13, the connector bay defining an aperture having at least two different heights.

15. The connector of claim 14, wherein a portion of the aperture bounding the first female coupler and the second female coupler defines a first height, and another portion of the aperture bounding the third female coupler defines a second height.

16. The connector of claim 15, the second height less than the first height.

17. A connector, comprising:
a body; and
a plurality of ports extending distally from a front major face of the body;
the body defining a connector bay configured to couple to any of:
 a single-tube, intermittent, deep vein thrombosis therapy male connector;
 a double-tube, intermittent, deep vein thrombosis therapy male connector; or
 a three-tube, sequential, deep vein thrombosis therapy male connector.

18. The connector of claim 17, further comprising one or more mechanical latch engagements configured receiving latches of the three-tube, sequential, deep vein thrombosis therapy male connector when the three-tube, sequential, deep vein thrombosis therapy male connector couples to the connector bay.

19. The connector of claim 17, further comprising visual indicia disposed on an exterior surface of the body.

20. The connector of claim 19, the visual indicia comprising an arrow indicating an airflow direction through the plurality of ports.

* * * * *